US007906303B2

(12) United States Patent
Ward (10) Patent No.: US 7,906,303 B2
(45) Date of Patent: Mar. 15, 2011

(54) **USE OF *RHIZOPUS* AMYLASES IN GRANULAR STARCH HYDROLYSIS**

(75) Inventor: Donald E. Ward, Cedar Rapids, IA (US)

(73) Assignee: Danisco US Inc., Palo Alto, CA (US)

( * ) Notice: Subject to any disclaimer, the term of this patent is extended or adjusted under 35 U.S.C. 154(b) by 0 days.

(21) Appl. No.: 12/399,813

(22) Filed: Mar. 6, 2009

(65) Prior Publication Data

US 2009/0253191 A1    Oct. 8, 2009

Related U.S. Application Data

(60) Provisional application No. 61/035,648, filed on Mar. 11, 2008.

(51) Int. Cl.
*C12P 7/10* (2006.01)
*C12P 1/00* (2006.01)
*C12P 7/06* (2006.01)
*C12N 9/30* (2006.01)

(52) U.S. Cl. ......... 435/165; 435/203; 435/267; 435/161
(58) Field of Classification Search ........................ None
See application file for complete search history.

(56) References Cited

U.S. PATENT DOCUMENTS

| 4,092,434 | A | 5/1978 | Yoshizumi et al. |
| 4,316,956 | A | 2/1982 | Lutzen |
| 4,514,496 | A | 4/1985 | Yoshizumi et al. |
| RE32,153 | E | 5/1986 | Tamura et al. |
| 4,587,215 | A | 5/1986 | Hirsh |
| 4,618,579 | A | 10/1986 | Dwiggins et al. |
| 6,352,851 | B1 | 3/2002 | Nielsen et al. |
| 7,037,704 | B2 | 5/2006 | Dunn-Coleman et al. |
| 7,413,887 | B2 | 8/2008 | Dunn-Coleman et al. |
| 2006/0148054 | A1* | 7/2006 | Fukuyama et al. ........... 435/161 |

FOREIGN PATENT DOCUMENTS

| WO | WO 84/02921 A2 | 8/1984 |
| WO | WO 92/00381 A1 | 1/1992 |
| WO | WO 99/28488 A2 | 6/1999 |
| WO | WO 00/04136 A1 | 1/2000 |
| WO | WO 2004/111218 A2 | 12/2004 |
| WO | WO 2005/052148 A2 | 6/2005 |
| WO | WO 2006/060062 | 10/2005 |
| WO | WO 2005/117756 A2 | 12/2005 |
| WO | WO 2006/069290 | 12/2005 |

OTHER PUBLICATIONS

Wang et al World J. of Micriobiol Biotechol., 2007, 23, 461-465.*
Altschul, S.F. et al. "Gapped BLAST and PSI-BLAST: a new generation of protein database search programs," *Nucleic Acids Research*, 25(17):3389-3402 (1997).
Boel, E. et al. "Glucoamylases G1 and G2 from *Aspergillus niger* are synthesized from two different but closely related mRNAs," *The EMBO Journal*, 3(5):1097-1102 (1984).
Chen, H.M. et al. "Substitution of asparagine residues in *Aspergillus awamori* glucoamylase by site-directed mutagenesis to eliminate N-glycosylation and inactivation by deamidation," *Biochem. J.*, 301, (Pt 1):275-281 (1994).
Chen, H.M. et al. "Identification and elimination by site-directed mutagenesis of thermolabile aspartyl bonds in *Aspergillus awamori* glucoamylase," *Protein Eng.*, 8(6):575-582, (1995).
Chen, H.-M. et al. "Effect of replacing helical glycine residues with alanines on reversible and irreversible stability and production of *Aspergillus awamori* glucoamylase," *Protein Eng.*, 9(6):499-505 (1996).
Hata, Y. et al. "The glucoamylase cDNA from *Aspergillus oryzae*: Its cloning, nucleotide sequence, and expression in *Saccharomyces cerevisiae*," *Agric. Biol. Chem.*, 55(4):941-949 (1991).
Jensen, B. et al. "Purification of extracellular amylolytic enzymes from the thermophilic fungus *Thermomyces lanuginosus*," *Can. J. Microbiol.*, 34(3):218-223 (1988).
Keim, C.R. "The wet milling process: the basis for corn wet milling alcohol production." In *The Alcohol Textbook: A reference for the beverage, fuel and industrial alcohol industries*, edited by K. Jacques et al., pp. 39-48. Nottingham, UK: Nottingham UK, (1999).
Kelsall, D.R. et al. "Grain dry milling and cooking for alcohol production: designing for 23% ethanol and maximum yield," In *The Alcohol Textbook: A reference for the beverage, fuel and industrial alcohol industries*, edited by K. Jacques et al., pp. 7-23. Nottingham, UK: Nottingham UK, (1999).
Miller, G.L. "Use of Dinitrosalicylic Acid Reagent for Determination of Reducing Sugar," *Anal. Chem.*, 31(3):426-428 (1959).
Pearson, W.R. et al. "Improved Tools for Biological Sequence Comparison," *Proc. Natl. Acad. Sci. USA*, 85(8):2444-2448 (1988).
Taylor, P.M. et al. "Some Properties of a Glucoamylase Produced by the Thermophilic Fungus *Humicola lanuginosa*," *Carbohydrate Research*, 61: 301-308 (1978).
Liakopoulou-Kyriakides, Maria et al., "Synergistic hydrolysis of crude corn starch by alpha-amylases and glucoamylases of various origins," *Ceral Chemistry, American Association of Cereal Chemists, Minneapolis, MN, US*, V. 78, N. 5, Sep. 1, 2001, pp. 603-607, XP008083292.
Peixoto, S. C. et al., "*Rhizopus microsporus var. rhizopodiformis*: A thermotolerant fungus with potential for production of thermostable amylases." *International Microbiology*, V. 6, N. 4, Dec. 2003, pp. 269-273, XP002536703.
Peixoto-Nogueira, S.C. et al., "Evidence of thermostable amylolytic activity from *Rhizopus microsporus var. rhizopodiformis* using wheat bran and corncob as alternative carbon source," *Bioprocess and Biosystems Engineering, Springer, Berlin, DE*, V. 31, N. 4, Oct. 17, 2007, pp. 329-334, XP019631456.
Shigechi, Hisayori et al., Direct production of ethanol from raw corn starch via fermentation by use of a novel surface-engineered yeast strain codisplaying glucoamylase and alpha-amylase, *Applied and Environmental Microbiology*, V. 70, N. 8, Aug. 2004, pp. 5037-5040, XP002536704.
International Search Report for International Application No. PCT/US2009/036283, mailed Jul. 29, 2009.

* cited by examiner

*Primary Examiner* — Delia M Ramirez
*Assistant Examiner* — Younus Meah (57) ABSTRACT

Described are compositions and methods relating to granular starch hydrolysis. Exemplary used for the compositions and methods are for ethanol production.

17 Claims, 5 Drawing Sheets

SEQUENCE LISTING

<160> NUMBER OF SEQ ID NOS: 2

<210> SEQ ID NO 1
<211> LENGTH: 402
<212> TYPE: PRT
<213> ORGANISM: Rhizopus spp.

<400> SEQUENCE: 1

```
Met Lys Ser Phe Leu Ser Leu Leu Cys Ser Val Phe Leu Leu Pro Leu
1               5                   10                  15

Val Val Gln Ser Val Pro Val Ile Lys Arg Ala Ser Ala Ser Asp Trp
            20                  25                  30

Glu Asn Arg Val Ile Tyr Gln Leu Leu Thr Asp Arg Phe Ala Lys Ser
        35                  40                  45

Thr Asp Asp Thr Asn Gly Cys Asn Asn Leu Ser Asp Tyr Cys Gly Gly
    50                  55                  60

Thr Phe Gln Gly Ile Ile Asn His Leu Asp Tyr Ile Ala Gly Met Gly
65                  70                  75                  80

Phe Asp Ala Ile Trp Ile Ser Pro Ile Pro Lys Asn Ala Asn Gly Gly
                85                  90                  95

Tyr His Gly Tyr Trp Ala Thr Asp Phe Ser Gln Ile Asn Glu His Phe
            100                 105                 110

Gly Thr Ala Asp Asp Leu Lys Lys Leu Val Ala Ala His Ala Lys
        115                 120                 125

Asn Met Tyr Val Met Leu Asp Val Val Ala Asn His Ala Gly Ile Pro
        130                 135                 140

Ser Ser Gly Gly Asp Tyr Ser Gly Tyr Thr Phe Gly Gln Ser Ser Glu
145                 150                 155                 160

Tyr His Thr Ala Cys Asp Ile Asn Tyr Asn Ser Gln Thr Ser Ile Glu
            165                 170                 175

Gln Cys Trp Ile Ser Gly Leu Pro Asp Ile Asn Thr Glu Asp Ser Ala
        180                 185                 190

Ile Val Ser Lys Leu Asn Ser Ile Val Ser Gly Trp Val Ser Asp Tyr
    195                 200                 205

Gly Phe Asp Gly Leu Arg Ile Asp Thr Val Lys His Ile Pro Leu Ala
210                 215                 220

Phe Leu Ile Leu Lys Met Glu Thr Leu Lys Asp Ile Asp Val Leu Val
225                 230                 235                 240

Asn Phe Ile Asp Asn His Asp Gln Pro Arg Leu Leu Ser Lys Ala Asp
                245                 250                 255

Gln Ser Leu Val Lys Asn Ala Leu Ala Tyr Ser Phe Met Val Gln Gly
            260                 265                 270

Ile Pro Val Leu Tyr Tyr Gly Thr Glu Gln Ser Phe Lys Gly Gly Asn
        275                 280                 285

Asp Pro Asn Asn Arg Glu Val Leu Trp Thr Thr Gly Tyr Ser Thr Thr
    290                 295                 300

Ser Asp Met Tyr Lys Phe Val Thr Thr Leu Val Lys Ala Arg Lys Gly
305                 310                 315                 320

Ser Asn Ser Thr Val Asn Met Gly Ile Ala Gln Thr Asp Asn Val Tyr
                325                 330                 335

Val Phe Gln Arg Gly Gly Ser Leu Val Val Asn Asn Tyr Gly Gln
            340                 345                 350

Gly Ser Thr Asn Thr Ile Thr Val Lys Ala Gly Ser Phe Ser Asn Gly
        355                 360                 365
```

```
Asp Thr Leu Thr Asp Val Phe Ser Asn Lys Ser Val Thr Val Gln Asn
    370                 375                 380

Asn Gln Ile Thr Phe Gln Leu Gln Asn Gly Asn Pro Ala Ile Phe Gln
385                 390                 395                 400

Lys Lys

<210> SEQ ID NO 2
<211> LENGTH: 599
<212> TYPE: PRT
<213> ORGANISM: Trichoderma reesei

<400> SEQUENCE: 2

Ser Val Asp Asp Phe Ile Ser Thr Glu Thr Pro Ile Ala Leu Asn Asn
1               5                   10                  15

Leu Leu Cys Asn Val Gly Pro Asp Gly Cys Arg Ala Phe Gly Thr Ser
                20                  25                  30

Ala Gly Ala Val Ile Ala Ser Pro Ser Thr Ile Asp Pro Asp Tyr Tyr
            35                  40                  45

Tyr Met Trp Thr Arg Asp Ser Ala Leu Val Phe Lys Asn Leu Ile Asp
50                  55                  60

Arg Phe Thr Glu Thr Tyr Asp Ala Gly Leu Gln Arg Arg Ile Glu Gln
65                  70                  75                  80

Tyr Ile Thr Ala Gln Val Thr Leu Gln Gly Leu Ser Asn Pro Ser Gly
                85                  90                  95

Ser Leu Ala Asp Gly Ser Gly Leu Gly Glu Pro Lys Phe Glu Leu Thr
            100                 105                 110

Leu Lys Pro Phe Thr Gly Asn Trp Gly Arg Pro Gln Arg Asp Gly Pro
        115                 120                 125

Ala Leu Arg Ala Ile Ala Leu Ile Gly Tyr Ser Lys Trp Leu Ile Asn
130                 135                 140

Asn Asn Tyr Gln Ser Thr Val Ser Asn Val Ile Trp Pro Ile Val Arg
145                 150                 155                 160

Asn Asp Leu Asn Tyr Val Ala Gln Tyr Trp Asn Gln Thr Gly Phe Asp
                165                 170                 175

Leu Trp Glu Glu Val Asn Gly Ser Ser Phe Phe Thr Val Ala Asn Gln
            180                 185                 190

His Arg Ala Leu Val Glu Gly Ala Thr Leu Ala Ala Thr Leu Gly Gln
        195                 200                 205

Ser Gly Ser Ala Tyr Ser Ser Val Ala Pro Gln Val Leu Cys Phe Leu
210                 215                 220

Gln Arg Phe Trp Val Ser Ser Gly Gly Tyr Val Asp Ser Asn Ile Asn
225                 230                 235                 240

Thr Asn Glu Gly Arg Thr Gly Lys Asp Val Asn Ser Val Leu Thr Ser
                245                 250                 255

Ile His Thr Phe Asp Pro Asn Leu Gly Cys Asp Ala Gly Thr Phe Gln
            260                 265                 270

Pro Cys Ser Asp Lys Ala Leu Ser Asn Leu Lys Val Val Val Asp Ser
        275                 280                 285

Phe Arg Ser Ile Tyr Gly Val Asn Lys Gly Ile Pro Ala Gly Ala Ala
290                 295                 300

Val Ala Ile Gly Arg Tyr Ala Glu Asp Val Tyr Tyr Asn Gly Asn Pro
305                 310                 315                 320

Trp Tyr Leu Ala Thr Phe Ala Ala Ala Glu Gln Leu Tyr Asp Ala Ile
                325                 330                 335
```

-continued

```
Tyr Val Trp Lys Lys Thr Gly Ser Ile Thr Val Thr Ala Thr Ser Leu
            340             345             350

Ala Phe Phe Gln Glu Leu Val Pro Gly Val Thr Ala Gly Thr Tyr Ser
            355             360             365

Ser Ser Ser Ser Thr Phe Thr Asn Ile Ile Asn Ala Val Ser Thr Tyr
    370             375             380

Ala Asp Gly Phe Leu Ser Glu Ala Ala Lys Tyr Val Pro Ala Asp Gly
385             390             395             400

Ser Leu Ala Glu Gln Phe Asp Arg Asn Ser Gly Thr Pro Leu Ser Ala
                405             410             415

Leu His Leu Thr Trp Ser Tyr Ala Ser Phe Leu Thr Ala Thr Ala Arg
            420             425             430

Arg Ala Gly Ile Val Pro Pro Ser Trp Ala Asn Ser Ser Ala Ser Thr
            435             440             445

Ile Pro Ser Thr Cys Ser Gly Ala Ser Val Val Gly Ser Tyr Ser Arg
            450             455             460

Pro Thr Ala Thr Ser Phe Pro Pro Ser Gln Thr Pro Lys Pro Gly Val
465             470             475             480

Pro Ser Gly Thr Pro Tyr Thr Pro Leu Pro Cys Ala Thr Pro Thr Ser
                485             490             495

Val Ala Val Thr Phe His Glu Leu Val Ser Thr Gln Phe Gly Gln Thr
            500             505             510

Val Lys Val Ala Gly Asn Ala Ala Ala Leu Gly Asn Trp Ser Thr Ser
            515             520             525

Ala Ala Val Ala Leu Asp Ala Val Asn Tyr Ala Asp Asn His Pro Leu
    530             535             540

Trp Ile Gly Thr Val Asn Leu Glu Ala Gly Asp Val Val Glu Tyr Lys
545             550             555             560

Tyr Ile Asn Val Gly Gln Asp Gly Ser Val Thr Trp Glu Ser Asp Pro
                565             570             575

Asn His Thr Tyr Thr Val Pro Ala Val Ala Cys Val Thr Gln Val Val
            580             585             590

Lys Glu Asp Thr Trp Gln Ser
            595
```

USE OF *RHIZOPUS* AMYLASES IN GRANULAR STARCH HYDROLYSIS

PRIORITY

The present application claims priority to U.S. Provisional Patent Application Ser. No. 61/035,648 filed on Mar. 11, 2008, which is hereby incorporated by reference in its entirety.

TECHNICAL FIELD

The compositions and methods relate to granular starch hydrolysis and are useful, e.g., in ethanol production.

INTRODUCTION

Amylases, particularly those having granular starch hydrolyzing (GSH) activity, such as alpha-amylase and glucoamylases, are important industrial enzymes used in processes to produce organic acids (e.g., lactic acids), amino acids (e.g., glutamic acids), alcohols (e.g., ethanol and butanol), and other compounds from starch containing substrates. Although a number of enzymes are commercially available for performing these processes, each has its own limitations and shortcomings. The need exist for improved amylases for industrial applications.

SUMMARY

The present compositions and methods relate to alpha-amylases obtained from *Rhizopus*, and/or combinations of these alpha-amylases with a glucoamylase, for the efficient hydrolysis of granular starch, facilitating the production of end products such as alcohols.

In one aspect, an enzyme composition comprising a *Rhizopus* spp. alpha-amylase is provided. In some embodiments, the alpha-amylase has at least 80% amino acid sequence identity to the sequence of SEQ ID NO. 1. In some embodiments, the alpha-amylase has at least 90% amino acid sequence identity to the SEQ ID NO. 1. In particular embodiments, the alpha-amylase has at least 91%, at least 92%, at least 93%, at least 94%, at least 95%, at least 96%, at least 97%, at least 98%, or even at least 99% amino acid sequence identity to the sequence of SEQ ID NO. 1. In some embodiments, the enzyme composition includes the *Rhizopus* spp. alpha-amylase as the only alpha-amylase, i.e., the only granular starch hydrolyzing component in the composition. In some embodiments, the composition is a cleaning composition, a detergent composition, a baking composition, an animal feed composition, or a starch hydrolyzing enzyme composition.

In some embodiments, the composition comprises a *Rhizopus* spp. alpha-amylase and at least one glucoamylase. In some embodiments, the glucoamylase is obtained from a strain of *Aspergillus, Talaromyces, Humicola* or *Trichoderma*. In some embodiments, the glucoamylase is a recombinant or engineered glucoamylase. In a particular embodiment, the glucoamylase is not a glucoamylase obtained from *Rhizopus oryzae*.

In some embodiments, the composition is added to or present in a fermentation medium. In some embodiments, the composition is added to or present in a baking composition, an animal feed composition, a cleaning composition or a starch hydrolysis composition.

In another aspect, a method of hydrolyzing a starch substrate is provided, comprising containing the starch substrate with a *Rhizopus* spp. alpha-amylase composition. In some embodiments, the starch is granular starch. In some embodiments, the granular starch is obtained from corn, wheat, rye, sorghum, and/or barley grain. In some embodiments, the starch is hydrolyzed at a temperature below the starch gelatinization temperature of the granular starch of the substrate.

In a related aspect, a method for producing alcohol is provided, comprising further contacting the hydrolyzed starch produced by contact with a *Rhizopus* spp. alpha-amylase composition with a microorganism capable of converting hydrolyzed starch (e.g., glucose) to alcohol. In particular embodiments, the alcohol is ethanol. In particular embodiments, the microorganism is a yeast capable of converting glucose to ethanol. In some embodiments, a method of producing ethanol is provided, comprising incubating granular starch with a *Rhizopus* spp. alpha-amylase composition and a microorganism capable of converting glucose to ethanol.

These and other features of the compositions and methods are described, below, with the aid of the accompanying drawings.

BRIEF DESCRIPTION OF THE DRAWINGS

The skilled artisan will understand that the drawings are for illustration purposes only and not intended to limit the scope of the present teachings.

DETAILED DESCRIPTION

I. Introduction

The present compositions and methods are based on the discovery that certain alpha-amylases obtained from *Rhizopus*, and/or combinations of these alpha-amylases with glucoamylase, can efficiently hydrolyze starch, particularly granular starch, facilitating the production of end products such as alcohols. Various aspects and embodiments of the compositions and methods are described in detail, following the definition of selected terms.

II. Definitions

Unless otherwise specified, all technical and scientific terms should be accorded their ordinary meaning as used in the relevant art. The following words and terms are defined for clarity:

As used herein, the term "starch" refers to a complex polysaccharide carbohydrates of plants. Starch molecules generally having the formula $(C_6H_{10}O_5)_x$, wherein X can be any number, and are predominantly in the forms of amylose and amylopectin.

As used herein, the term "granular starch" refers to raw starch that has not been subject to the temperature of gelatinization.

As used herein, the terms "granular starch hydrolyzing enzyme" ("GSHE") or "enzyme having granular starch hydrolyzing (GSH) activity" refer to enzymes that have the ability to hydrolyze starch in granular form.

As used herein, the term "alpha-amylase" refers to enzymes that catalyze the hydrolysis of alpha-1,4-glucosidic linkages. The enzymes are classified as EC 3.2.1.1. These enzymes have also been described as those effecting the exo or endohydrolysis of 1,4-alpha-D-glucosidic linkages in polysaccharides containing 1,4-.alpha-linked D-glucose units. Another term used to describe these enzymes is "glycogenase."

As used herein, the term "glucoamylase" refers to the amyloglucosidase class of enzymes (e.g., EC 3.2.1.3, glucoamylase, 1,4-alpha-D-glucan glucohydrolase). These are exo-acting enzymes, which release glucosyl residues from the non-reducing ends of amylose and amylopectin molecules. The enzyme also hydrolyzes alpha-1,6 and alpha-1,3 linkages although at much slower rate than alpha-1,4 linkages.

As used herein, the term "oligosaccharides" refers to any compound having 2 to 10 monosaccharide units joined in glycosidic linkages. These short chain polymers of simple sugars include dextrins.

As used herein, the term "DE" or "dextrose equivalent" is an industry standard for measuring the concentration of total reducing sugars, calculated as D-glucose on a dry weight basis. Unhydrolyzed granular starch has a DE that is essentially 0 and D-glucose has a DE of 100.

As used herein, the term "total sugar content" refers to the total sugar content present in a starch composition.

As used herein, the term "dry solids," or "ds," refers to the total solids of a slurry in % on a dry weight basis.

As used herein, the term "starch binding domain (SBD)" refers to an amino acid sequence that binds preferentially to a starch (polysaccharide) substrate.

As used herein, the term "catalytic domain" refers to a structural region of a polypeptide which is distinct from the SBD and which contains the active site for substrate hydrolysis.

As used herein, the term "truncated alpha-amylase" refers to an alpha-amylase, where at least part of the starch binding domain has been eliminated.

As used herein, the term "saccharification" refers to enzymatic conversion of starch to glucose.

The term "liquefaction" refers to the stage in starch conversion in which gelatinized starch is hydrolyzed to give low molecular weight soluble dextrins. The term "degree of polymerization" (DP) refers to the number (n) of anhydroglucopyranose units in a given saccharide. Examples of DP1 are the monosaccharides glucose and fructose. Examples of DP2 are the disaccharides maltose and sucrose. For purposes herein "comparable liquefaction processes" are those conducted under comparable conditions, preferably conditions standardized for temperature, pH, substrate concentration, calcium ion concentration and the like. Preferably comparable liquefaction processes are compared on an equal protein or equal activity units basis, however, is some embodiments, either protein, or activity units, or both may vary in comparable liquefaction processes. The skilled artisan will understand the bases on which liquefaction processes may be "comparable".

During liquefaction processes, the viscosity of the starch slurry is frequently used as a measure of the conversion of the starch into smaller DP units. Sometimes herein the expression "initial viscosity" is used. The skilled artisan will appreciate that this is a term of art, and what is intended is not literally the initial viscosity, but rather the peak viscosity which occurs for example at around the point of gelatinization of the substrate. Initial viscosity is used to distinguish from the "final viscosity" which is the viscosity of a substrate, e.g., starch slurry, at the conclusion of a liquefaction process. Thus, as is apparent from looking at a graph of the viscosity over the time-course of a liquefaction process, the initial or peak viscosity occurs not immediately, but after a certain passage of time, e.g., less than 50% of the overall time, and more preferably within about the first $\frac{1}{3}$ or even $\frac{1}{4}$ or $\frac{1}{5}$ of the total time of liquefaction. For example, in a liquefaction exemplified herein, the peak viscosity typically occurs within the first ten minutes, after which time the enzyme is added and the viscosity begins to drop. As the starch granules open up during the gelatinization process, the interior of the granules become more accessible to the amylase activity and more cleavage, resulting in a drop in viscosity.

As used herein, the phrase "simultaneous saccharification and fermentation (SSF)" refers to a process in the production of end-products in which a microbial organism, such as an ethanol producing microorganism and at least one enzyme such as an amylase are in the same process step. SSF may also refer to the contemporaneous hydrolysis of granular starch substrates to saccharides, including glucose, and the fermentation of the saccharides into alcohol, in the same reactor vessel.

As used herein, the term "contacting" refers to the placing of the respective entities (e.g, enzymes, substrates, buffers, and the like) in sufficiently close proximity to allow a reaction to occur, such as the enzymatic conversion of a substrate to an end-product. The enzymes, substrates, or other entities may be in solution or suspension, and contacting may refer to mixing the solutions or suspensions.

As used herein, the term "enzymatic conversion" generally refers to the modification of a substrate by enzymatic action. The term particularly includes the modification of a granular starch substrate by the action of an enzyme.

As used herein, the term "degree of polymerization (DP)" refers to the number (n) of anhydroglucopyranose units in a given saccharide. Monosaccharides, such as glucose and fructose, are referred to as DP-1. Disaccharides, such as maltose and sucrose, are referred to as DP-2. DP>3 denotes polymers with a degree of polymerization of greater than 3.

As used herein, the terms "end-product" or "desired end-product" refer to a molecule produced by the enzymatic conversion of a starch substrate.

As used herein, the term "dry solids content (ds)" refers to the total solids of a slurry in terms of % on a dry weight basis (i.e., % wt/wt).

As used herein, the term "slurry" refers to an aqueous mixture containing insoluble solids.

As used herein, the term "residual starch" refers to the starch (soluble or insoluble) remaining in a composition after fermentation of a starch-containing substrate present in the composition.

As used herein, the term "mash" refers to a mixture of fermentable carbon molecules (e.g., carbohydrates) in water, which can be used to produce a fermented product, such as an alcohol.

As used herein, the term "stillage" refers to a mixture of non-fermented solids and water, which is the residue after removal of alcohol from a fermented mash.

As used herein, the terms "distillers dried grain (DDG)" and "distillers dried grain with solubles (DDGS)" refer to a useful by-product of grain fermentation.

As used herein, the terms "ethanol producer," "ethanol-producing microorganism," or "ethanologenic microorganism," refer to a microorganism with the ability to convert a sugar or oligosaccharide to ethanol. The ethanologenic microorganisms are ethanologenic by virtue of their ability to express one or more enzymes that individually or together convert sugar to ethanol.

As used herein, the terms "recovered," "isolated," and "separated" refer to a compound, protein, cell, nucleic acid or amino acid that is removed from at least one component with which it is naturally associated.

As used herein, the terms "transformed," "stably transformed," and "transgenic," with reference to a cell, mean that the cell has a non-native (e.g., heterologous) nucleic acid sequence integrated into its genome or carried as an episomal plasmid that is maintained through multiple generations.

As used herein, the term "specific activity" refers to the amount of substrate converted to product by a given amount of enzyme in a given amount of time under specific conditions. Specific activity is often expressed as units (U)/mg of protein.

As used herein, the term "enzyme unit (U)" refers to the amount of enzyme that produces 1 µmole of product per minute under specified assay conditions. For example, the term "glucoamylase activity unit" ("GAU") is defined as the amount of enzyme required to produce 1 g of glucose per hour from soluble starch substrate (4% ds) under assay conditions of 60° C. and pH 4.2. In another example, a granular starch hydrolyzing enzyme unit (GSHE U) is the amount of GSHE required to produce 1 mg of glucose per minute from granular starch under assay conditions of, for example 25° C. at pH 5.0. In some embodiments, a GSHE U is the amount of a GSHE required to produce 1 mg glucose/min from a granular starch substrate at 50° C. at pH 4.5.

As used herein, the term "yield" refers to the amount of end-product or desired end-products produced in a reaction. Yield may refer to the amount of product in grams or moles, the volume of product in mls, the concentration of the product in g/L or moles/L, or the like.

As used herein, the terms "protein" and "polypeptide" are used interchangeably to refer to a molecule made up of a single chain of amino acid residues linked by peptide bonds. The conventional one-letter or three-letter code for amino acid residues is used herein. Unless otherwise specified, all polypeptides are written in the stand N-terminal to C-terminal direction.

As used herein, the term "nucleic acid" and "polynucleotide" are used interchangeably to refer to polymers of nucleotides, including DNA, RNA, cDNA, DNA/RNA hybrids, or chemically modified nucleic acids. Nucleic acids may be single stranded or double stranded. Because the genetic code is degenerate, more than one codon may be used to encode a particular amino acid, and the present invention encompasses all polynucleotides, which encode a particular amino acid sequence. Unless otherwise specified, all polynucleotides are written in the stand 5' to 3' direction.

As used herein, the term "heterologous," with reference to a polynucleotide or polypeptide, refers to a polynucleotide or polypeptide that does not naturally occur in a given host cell, or is expressed naturally under the control of different regulatory element in the host cell.

As used herein, the term "homologous," with reference to a polynucleotide or polypeptide, refers to a polynucleotide or polypeptide that occurs naturally in the host cell.

As used herein, the term "gene" refers to a polynucleotide sequence (e.g., a DNA segment) encoding a particular polypeptide chain, optionally in combination with any of the regulatory and control elements, preceding and following the coding sequence, e.g. a 5' untranslated (5' UTR) or "leader" sequences, a 3' UTR or "trailer" sequences, intervening sequences (introns) between individual coding segments (exons), RNA polymerase binding sequences, promoters, enhancers, terminators, and the like.

As used herein, the term "recombinant," when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified or that a protein is expressed in a non-native or genetically modified environment, e.g., in an expression vector for a prokaryotic or eukaryotic system. Thus, for example, recombinant cells express nucleic acids or polypeptides that are not found within the native (non-recombinant) form of the cell or express native genes that are otherwise abnormally expressed, under expressed, over expressed or not expressed at all.

As used herein, the term "expression" refers to the process by which a polypeptide is produced based on the nucleic acid sequence of a gene. The process includes both transcription and translation.

As used herein, the term "vector," "DNA construct," "transforming DNA," and the like refer to a polynucleotide that can be transiently or stably introduced into one or more cell types. Vectors include cloning vectors, expression vectors, shuttle vectors, plasmids, cassettes and the like.

As used herein, the term "introduced" in the context of inserting a nucleic acid sequence into a cell, means "transfection," "transformation," or "transduction," and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

As used herein, the term "derived" encompasses the terms "originated from," "obtained," "obtainable from," and "isolated from."

As used herein, the terms "host cell" or "host strain" refer to a cell that contains a vector and supports the replication, and/or transcription of the vector, e.g., to express a polypeptide of interest. Host cells include bacteria, yeast, filamentous fungi, plant cells, and animal cells.

As used herein, the term "filamentous fungi" refers to eukaryotic microorganisms including filamentous forms of the subdivision Eumycotina. These fungi are characterized by having a vegetative mycelium composed of chitin, cellulose, and other complex polysaccharides. Filamentous fungi are morphologically, physiologically, and genetically distinct from yeasts. Exemplary filamentous fungi are *Trichoderma* spp., which have previously been classified as *Hypocrea* spp. Exemplary *Trichoderma* spp. include *Trichoderma longibrachiatum, Trichoderma reesei, Trichoderma viride*, and *Hypocrea jecorina*.

As used herein, the term "wild-type (wt)" refers to an organism, nucleic acid or protein that is native or naturally occurring. In many cases, a wt organism, nucleic acid or protein, serves as the "parent" for making or identifying mutants or variants.

As used herein, the term "parent" refers to an organism, nucleic acid or protein that is used as the basis for making or identifying mutants or variants.

As used herein, the term "mutant" or "variant" refers to a an organism, nucleic acid or protein derived from a parent organism, nucleic acid or protein, but including at least one genetic or biochemical change with respect to the parent. For example, where the mutant or variant is a polypeptide, it includes at least one amino acid substitution, deletion, or insertion relative to the parent polypeptide, or is chemically modified with respect to the parent polypeptide. Where the mutant or variant is a polynucleotide, it includes at least one bases substitution, deletion, or insertion relative to the parent polynucleotide, or is chemically modified with respect to the parent polynucleotide. Where the mutant or variant is an organism, it includes at least one polynucleotide of polypeptide not found in the parent organism.

A variant polynucleotide or polypeptide may have a certain percent sequence identity (e.g., at least 65%, at least 70%, at least 75%, at least 80%, at least 85%, at least 90%, at least 91%, at least 92%, at least 93%, at least 94%, at least 95%, at least 96%, at least 97%, at least 98%, and even at least 99%) with a parent polynucleotide or polypeptide, such that, when aligned, that percentage of bases or amino acid residues are the same in comparing the two sequences. This alignment and the percent homology or identity can be determined using any suitable software program known in the art, for example, those described in CURRENT PROTOCOLS IN MOLECULAR BIOLOGY (Ausubel F. M. et al., (eds) 1987, Supplement 30, section 7.7.18). These programs include the GCG Pileup program, FASTA (Pearson et al., (1988) *Proc. Natl. Acad. Sci. USA* 85:2444 2448) and BLAST (BLAST Manual, Altschul et al., Natl Cent. Biotechnol. Inf., Natl Lib. Med. (NCIB NLM NIH), Bethesda, Md., and Altschul et al., (1997) *Nucleic Acids Res.* 25:3389 3402). Other alignment programs includeALIGN Plus (Scientific and Educational Software, PA), preferably using default parameters, and the TFASTA Data Searching Program available in the Sequence Software Package Version 6.0 (Genetics Computer Group, University of Wisconsin, Madison, Wis.).

Variant polynucleotides may additionally or alternatively be complementary to sequences of a parent polynucleotide (or the complement, thereof), such that they may be identified through hybridizing. As used herein, stringent conditions are 50° C. and 0.2×SSC (1×SSC=0.15 M NaCl, 0.015 M sodium citrate, pH 7.0) and highly stringent conditions are 65° C. and 0.1×SSC, although other buffer systems and temperatures may be used for hybridization. Hybridization and washing conditions are well known in the art, as exemplified by Chapters 9 and 11 of Sambrook et al. (1989).

The singular forms "a," "an," and "the" include plural referents unless the context clearly dictates otherwise. Thus, for example, reference to "an enzyme" includes a plurality of such enzymes, and reference to "the formulation" includes reference to one or more formulations and equivalents thereof known to those skilled in the art, and so forth.

"SPEZYME® FRED" is a commercially available enzyme preparation produced by Genencor, International, that includes as an active ingredient an engineered variant of the *B. licheniformis* α-amylase having the substitutions M15T, H133Y, N188S, and A209V. The specific activity is a minimum of 17,400 AAU/g.

The term "about" with respect to a numerical value or range indicates that the numerical value can be 10% greater or less than the stated value. In other embodiments, "about" indicates that a numerical value can be 5% greater or less than the stated value.

Numeric ranges are inclusive of the numbers defining the range.

III. Composition and Methods Involving Alpha-Amylases Obtained from *Rhizopus* Spp The present compositions and methods are based on the discovery that certain alpha-amylases obtained from *Rhizopus* spp., and/or combinations of these *Rhizopus* alpha-amylases with glucoamylase, can efficiently hydrolyze starch to assist in the production of end products such as alcohols. The *Rhizopus* alpha-amylase compositions are particularly effective for use with granular starch, which has no been subjected to its gelatinization temperature. Aspects and embodiments of the compositions and methods include those described, below.

In a first aspect, a composition that includes a *Rhizopus* spp. alpha-amylase polypeptide is provided. The *Rhizopus* spp. alpha-amylase polypeptide may be the only alpha-amylase polypeptide present in the composition, or the composition may include one or more additional alpha-amylase polypeptides. In this manner the composition may consist essentially of a *Rhizopus* spp. alpha-amylase polypeptide. The composition can be added to raw starch containing plant material to affect starch hydrolysis and/or alcohol production, wherein the *Rhizopus* spp. alpha-amylase polypeptide functions as a granular starch hydrolyzing component in the composition.

In some embodiments, the alpha-amylase is from a *Rhizopus* spp., e.g., *Rhizopus achlamydosporus, Rhizopus arrhizus, Rhizopus azygosporus, Rhizopus chinensis, Rhizopus delemar, Rhizopus formosaensis, Rhizopus japonicus, Rhizopus javanicus, Rhizopus microsporus, Rhizopus nigricans, Rhizopus niveus, Rhizopus oligosporus, Rhizopus oryzae, Rhizopus pygmaeus, Rhizopus rhizopodiformis, Rhizopus schipperae, Rhizopus semarangensis, Rhizopus sontii, Rhizopus stolonifer, Rhizopus thermosus, Rhizopus tonkinensis, Rhizopus tritici* or *Rhizopus usamii*. In some embodiments, the *Rhizopus* alpha-amylase is a *Rhizopus oryzae* alpha-amylase.

In some embodiments, the *Rhizopus* alpha-amylase is a recombinant alpha-amylase. The sequence of the recombinant alpha-amylase may optionally be altered from that of a naturally-occurring *Rhizopus* alpha-amylase. The recombinant alpha-amylase is typically expressed in a suitable host cell, which are genetically engineered to express the *Rhizopus* alpha-amylase. In some embodiments, filamentous fungal cells are used as host cells. Exemplary filamentous fungal hosts are *Aspergillus* spp., *Trichoderma* spp., a *Fusarium* spp., a *Penicillium* spp., or a *Rhizopus* spp. Exemplary fungal host cells include, but are not limited to, *A. nidulans, A. awamori, A. oryzae, A. aculeatus, A. niger, A. japonicus, A. kawachi, T. reesei, T. viride, F. oxysporum, F. solani*, and *R. oryzae*. Methods of expressing recombinant polypeptides, including, vectors that can be used as well as the transformation and culturing of host cells are known in the art and disclosed in publications, e.g., WO 2005/117,756.

In some embodiments, the alpha-amylase has an amino acid sequence that is substantially identical to the amino acid sequence of SEQ ID NO: 1 shown, below. This sequence corresponds to the exemplary *Rhizopus* alpha-amylase.

```
MKSFLSLLCSVFLLPLVVQSVPVIKRASASDWENRVIYQLLTDRFAKSTD

DTNGCNNLSDYCGGTFQGIINHLDYIAGMGFDAIWISPIPKNANGGYHGY

WATDFSQINEHFGTADDLKKLVAAAHAKNMYVMLDVVANHAGIPSSGGDY

SGYTFGQSSEYHTACDINYNSQTSIEQCWISGLPDINTEDSAIVSKLNSI

VSGWVSDYGFDGLRIDTVKHIPLAFLILKMETLKDIDVLVNFIDNHDQPR

LLSKADQSLVKNALAYSFMVQGIPVLYYGTEQSFKGGNDPNNREVLWTTG

YSTTSDMYKFVTTLVKARKGSNSTVNMGIAQTDNVYVFQRGGSLVVVNNY

GQGSTNTITVKAGSFSNGDTLTDVFSNKSVTVQNNQITFQLQNGNPAIFQ

KK
```

In some embodiments, the alpha-amylase amino acid sequence has at least 85%, at least 90%, at least 95%, at least 96%, at least 97%, at least 98% or at least 99% sequence identity to the amino acid sequence of SEQ ID NO: 1. In some embodiments, the alpha-amylase has an amino acid sequence that is 90% identical to the amino acid sequence of SEQ ID NO: 1. In some embodiments, the alpha-amylase has an amino acid sequence that is 95% identical to the amino acid sequence of SEQ ID NO: 1. In some embodiments, the alpha-amylase has an amino acid sequence that is 97% identical to the amino acid sequence of SEQ ID NO: 1. In some embodiments, the alpha-amylase has an amino acid sequence that is 99% identical to the amino acid sequence of SEQ ID NO: 1. In some embodiments, the alpha-amylase has the amino acid sequence of SEQ ID NO: 1. In some embodiments, the alpha-amylase has granular starch hydrolyzing (GSH) activity, which may be determined as described, herein. In some embodiments, the alpha-amylase has GSH activity that is at least 65%, at least 70%, at least 75%, at least 80%, at least 85%, at least 90%, at least 95%, at least 96%, at least 97%, at least 98% or even at least 99% of that of the GSH activity of the alpha-amylase having the sequence of SEQ ID NO: 1.

In some embodiments, an amino acid sequence having at least 70% at least 80% at least 85%, or even at least 90% or more sequence identity to the sequence of SEQ ID NO: 1 will include conservative amino acid substitutions using L-amino acids, wherein one amino acid is replaced by another biologically similar amino acid. Conservative amino acid substitutions are those that preserve the general charge, hydrophobicity/hydrophilicity, and/or steric bulk of the amino acid being substituted. Non-limiting examples of conservative substitutions include those between the following groups: Gly/Ala, Val/Ile/Leu, Lys/Arg, Asn/Gln, Glu/Asp, Ser/Cys/Thr and Phe/Trp/Tyr. Other conservative substitutions can be taken from the table below.

TABLE 1

Conservative Amino Acid Replacements

| For Amino Acid | Code | Replace with any of |
| --- | --- | --- |
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, b-Ala, Acp |
| Isoleucine | I | D-Ile, Val, D-Val, Leu, D-Leu, Met, D-Met |
| Leucine | L | D-Leu, Val, D-Val, Leu, D-Leu, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, D-Trp, Trans-3,4, or 5-phenylproline, cis-3,4, or 5-phenylproline |
| Proline | P | D-Pro, L-I-thioazolidine-4-carboxylic acid, D-or L-1-oxazolidine-4-carboxylic acid |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

In other embodiments, the amino acid substitutions are not conservative substitutions.

In some embodiments, the alpha-amylase is a fragment of an amino acid sequence comprising at least 70%, at least 80%, at least 85%, at least 90%, at least 91%, at least 92%, at least 93%, at least 94%, at least 95%, at least 96%, at least 97%, at least 98%, or even at least 99% sequence identity to SEQ ID NO: 1, wherein the fragment comprises at least 350 amino acids, at least 375 amino acids, or even at least 390 amino acids. The fragment preferably has GSH activity that is at least 65%, at least 70%, at least 75%, at least 80%, at least 85%, at least 90%, at least 95%, at least 96%, at least 97%, at least 98% or even at least 99% of that of the GSH activity of the alpha-amylase having the sequence of SEQ ID NO: 1, which may be determined using the assays described, herein. In some embodiments, the fragment of the alpha-amylase does not have a starch binding domain, or includes a truncated starch binding domain.

In some embodiments, the composition further includes one or more glucoamylases. The selection of the particular glucoamylase (or plurality of glucoamylases) is generally not believed to be critical. Suitable glucoamylases include naturally occurring wild-type glucoamylases as well as variant and genetically engineered mutant/variant glucoamylases, including hybrid or chimeric glucoamylases. Numerous suitable glucoamylases are endogenously expressed by bacteria, plants and fungus, and many have been cloned and heterologously expressed in the same or different organisms. In particular embodiments, a filamentous fungal glucoamylase is used. Where the *Rhizopus* spp. alpha-amylase polypeptide is the only alpha-amylase polypeptide present in the composition, the composition can be said to consist essentially of a *Rhizopus* spp. alpha-amylase polypeptide, along with a glucoamylase.

Exemplary glucoamylases that can be used in the present compositions and methods include *Aspergillus niger* G1 and G2 glucoamylase (Boel et al. (1984) *EMBO J.* 3:1097-1102, WO 92/00381, WO 00/04136, and U.S. Pat. No. 6,352,851); *Aspergillus awamori* glucoamylases (WO 84/02921); *Aspergillus oryzae* glucoamylases (Hata et al. (1991) *Agric. Biol. Chem.* 55:941-949); and *Aspergillus shirousami* glucoamylases (Chen et al., (1996) *Prot. Eng.* 9:499-505; Chen et al. (1995) *Prot. Eng.* 8:575-582; and Chen et al., (1994) *Biochem J.* 302:275-281). Useful glucoamylases are also obtained from strains of *Talaromyces* such as those derived from *T. emersonii*, *T. leycettanus*, *T. duponti* and *T. thermophilus* (WO 99/28488, U.S. Pat. Nos. RE 32,153 and 4,587, 215); strains of *Trichoderma*, such as *T. reesei*, and particularly glucoamylases having at least 80%, at least 85%, at least 90%, at least 91%, at least 92%, at least 93%, at least 94%, at least 95%, at least 96%, at least 97%, at least 98%, and even at least 98% amino acid sequence identity to SEQ ID NO: 4 disclosed in U.S. Pat. Pub. No. 2006-0094080; strains of *Rhizopus*, such as *R. niveus* and *R. oryzae*; strains of *Mucor* and strains of *Humicola*, such as *H. grisea* (Boel et al. (1984) *EMBO J.* 3:1097-1102, WO 92/00381, WO 00/04136, Chen et al., (1996) *Prot. Eng.* 9:499-505, Taylor et al. (1978) Carbohydrate Res. 61:301-308, U.S. Pat. Nos. 4,514,496, 4,092, 434, 4,618,579, Jensen et al. (1988) *Can. J. Microbiol.* 34:218-223, and SEQ ID NO: 3 of WO 2005/052148). In some embodiments, the glucoamylase will have at least 85%, at least 90%, at least 91%, at least 92%, at least 93%, at least 94%, at least 95%, at least 96%, at least 97%, at least 98% and even at least 99% sequence identity to the amino acid sequence of SEQ ID NO: 3 of WO 05/052148. Other glucoamylases include those obtained from *Athelia rolfsii* and variants thereof (WO 04/111218).

Enzymes having glucoamylase activity and that are used commercially are produced from, for example, *Aspergillus*

*niger* (trade name DISTILLASE, OPTIDEX L-400 and G ZYME G990 4× from Danisco US, Inc, Genencor Division.) and *Rhizopus* spp. (trade name CU.CONC from Shin Nihon Chemicals, Japan). Additional enzymes include three forms of glucoamylase (E.C.3.2.1.3) of a *Rhizopus* sp., namely "Gluc1" (MW 74,000), "Gluc2" (MW 58,600), and "Gluc3" (MW 61,400).

In some embodiments, the glucoamylase used in the compositions and methods encompassed by the invention has an amino acid sequence that is substantially identical to the amino acid sequence of SEQ ID NO: 2, shown, below. This sequence corresponds to the exemplary glucoamylase, TrGA.

```
SVDDFISTETPIALNNLLCNVGPDGCRAFGTSAGAVIASPSTIDPDYYYM

WTRDSALVFKNLIDRFTETYDAGLQRRIEQYITAQVTLQGLSNPSGSLAD

GSGLGEPKFELTLKPFTGNWGRPQRDGPALRAIALIGYSKWLINNNYQST

VSNVIWPIVRNDLNYVAQYWNQTGFDLWEEVNGSSFFTVANQHRALVEGA

TLAATLGQSGSAYSSVAPQVLCFLQRFWVSSGGYVDSNINTNEGRTGKDV

NSVLTSIHTFDPNLGCDAGTFQPCSDKALSNLKVVVDSFRSIYGVNKGIP

AGAAVAIGRYAEDVYYNGNPWYLATFAAAEQLYDAIYVWKKTGSITVTAT

SLAFFQELVPGVTAGTYSSSSSTFTNIINAVSTYADGFLSEAAKYVPADG

SLAEQFDRNSGTPLSALHLTWSYASFLTATARRAGIVPPSWANSSASTIP

STCSGASVVGSYSRPTATSFPPSQTPKPGVPSGTPYTPLPCATPTSVAVT

FHELVSTQFGQTVKVAGNAAALGNWSTSAAVALDAVNYADNHPLWIGTVN

LEAGDVVEYKYINVGQDGSVTWESDPNHTYTVPAVACVTQVVKEDTWQS
```

The sequence of the recombinant glucoamylase can, but need not be altered from that of a naturally-occurring glucoamylase.

The recombinant glucoamylase may be expressed in a host cell, including but are not limited to an *Aspergillus* spp. (e.g., *Aspergillus kawachi*), *Rhizopus* spp. (e.g., *Rhizopus oryzae*), or *Trichoderma* spp. (e.g., *Trichoderma reesei*) cell.

In some embodiments, the present compositions include a *Rhizopus* spp. alpha-amylase having an amino acid sequence with at least 90%, at least 95%, at least 96%, at least 97%, at least 98% or at oven least 99% sequence identity to the amino acid sequence of SEQ ID NO: 1 and a glucoamylase that is not a *Rhizopus* glucoamylase. In some embodiments, the present compositions include a *Rhizopus* spp. alpha-amylase having an amino acid sequence with at least 90%, at least 95%, at least 96%, at least 97%, at least 98% or at oven least 99% sequence identity to the amino acid sequence of SEQ ID NO: 1 and a glucoamylase that is a wild type or variant *Aspergillus, Trichoderma*, of Talaromyces, or *Humicola* glucoamylase.

In some embodiments, the ratio of the alpha-amylase activity (SSU or AAU) to glucoamylase activity (GAU) in the compositions is about 20:1 to about 1:20, about 15:1 to about 1:15, about 10:1 to about 1:10, about 5:1 to about 1:5, or about 4:1 to about 1:4.

In some embodiments, the compositions above which include an alpha-amylase and a glucoamylase also include additional enzymes, including but are not limited to, proteases, cellulases, phytases, pullulanases, other alpha-amylases, glucoamylases, and combinations thereof. Exemplary additional (or second) alpha-amylases include those isolated from *Geobacillus stearothermophilus, Bacillus licheniformis, Bacillus amyloliquefaciens, Bacillus subtilis, Bacillus* sp. TS-23, and the like. Commercially available enzymes include SPEZYME® FRED and SPEZYME® ETHYL produced by Genencor, International. Where the composition includes a second alpha-amylases, the *Rhizopus* spp. alpha-amylase imparts advantageous features to the composition compared to the composition in the absence of the *Rhizopus* spp. alpha-amylase.

In some embodiments, the composition is a fermentation medium, a cleaning composition, a detergent composition, a baking composition, an animal feed composition, or a starch conversion enzyme composition. In some embodiments, the compositions are useful in performing starch conversion, and particularly in hydrolyzing granular starch.

In another aspect, a method of using a *Rhizopus* spp. alpha-amylase is provided. In some embodiments, the methods include contacting a substrate containing granular starch with a composition that includes a *Rhizopus* spp. alpha-amylase. Substrates containing granular starch include grains such as wheat, corn (maize), rye, sorghum (milo), rice, millet, barley, triticale, and combinations thereof. Other substrates include cassaya (tapioca), potato, sweet potato, sugar beets, sugarcane, and legumes such as soybean and peas.

In some embodiments, whole grain may be used as a source of granular starch. Whole grains include corn, wheat, rye, barley, sorghum, and combinations thereof. In other embodiments, granular starch may be obtained from fractionated cereal grains including fiber, endosperm and/or germ components. In some embodiments, plant material obtained from different sources may be mixed together to obtain substrates (e.g., corn and milo or corn and barley). Preferably the substrates are in the form of a slurry.

Methods for fractionating plant material, such as corn and wheat, are known in the art. In some embodiments, plant material is prepared by means such as milling. Two general milling processes are wet milling or dry milling. Methods of milling are well known and reference is made TO THE ALCOHOL TEXTBOOK: A REFERENCE FOR THE BEVERAGE, FUEL AND INDUSTRIAL ALCOHOL INDUSTRIES 3$^{rd}$ ED. K. A. Jacques et al. (eds) (1999) Nottingham University Press., see, e.g., Chapters 2 and 4.

In some embodiments, the plant material reduced by milling or other means is combined with a solution to produce a slurry comprising a granular starch substrate. In some embodiments, the slurry includes a side stream from starch processing such as backset. In some embodiments, the slurry comprises about 15 to about 55% ds (e.g., 20-50%, 25-45%, 25-40%, 20-35%, and 30-35%).

In some embodiments, the method involves contacting a slurry that includes a granular starch substrate with *Rhizopus* spp. alpha-amylase composition. The contacting may be for a period of 15 minutes to about 20 hours (e.g., from about 30 min to 10 hrs, or from 30 min to 5 hrs). The pH is typically maintained at pH 4.0 to less than about 6.5. In some embodiments, the contacting occurs at a temperature of about 60° C. to about 120° C., e.g., from about 60° C. to about 85° C., from about 40° C. to about 85° C., and from about 50° C. to about 80° C., for a sufficient time to hydrolyze the starch.

In some embodiments, the contacting occurs at a temperature about 0 to 30° C. below the starch gelatinization temperature. This temperature may be about 0 to about 25° C., about 0 to about 20° C., about 0 to about 15° C., and even about 0 to about 10° C. below the starch gelatinization temperature. The particular temperature will vary and depends on the type of granular starch in the slurry. For example, the starch gelatinization temperature of corn is generally higher than the starch gelatinization temperature of wheat or rye. In some embodiments, the temperature is between about 45 to about 80° C., between about 50 to about 75° C., or between about 50 to about 70° C. In some embodiments the temperature is about 65° C., below about 62° C., below about 60° C., or below about 55° C. In other embodiments the temperature is above about 40° C., above about 45° C., above about 50° C., or above about 55° C.

An effective amount of a *Rhizopus* spp. alpha-amylase can be determined by a skilled person, e.g., using the assays described, herein. In some embodiments, the amount is from about 0.1 to about 50 AAU/g ds, including about 0.1 to about 15 AAU/g ds, about 0.1 to about 10 AAU/g ds, and about 0.1 to about 5 AAU/g ds.

In some embodiments, the slurry is exposed to a liquefaction step including an increase in temperature, such as about 0° to about 45° C. above the starch gelatinization temperature (e.g., to 65° C. to 120° C., 70° C. to 110° C., 70° C. to 90° C.) for a period of time of about 2 minutes to about 6 hours (e.g., about 2 minutes to about 4 hrs) at a pH of about 4.0 to about 6.0. The temperature can be increased by a conventional high temperature jet cooking system for a short period of time for completing the gelatinization of the granular starch. The gelatinized starch can be further hydrolyzed at a temperature ranging from about 75° C. to about 95° C., in some embodiments between about 80° C. and about 85° C. for a period of about 30 to about 120 minutes. In some embodiments, a second dose of an alpha-amylase can be added to the liquefaction step. In other embodiments, no additional alpha-amylase is added. In some embodiments, the additional dose includes a *Rhizopus* spp. alpha-amylase. In some embodiments, the *Rhizopus* spp. alpha-amylase is the only alpha-amylase used in the additional dose.

The method further includes saccharifying the liquefied substrate with a glucoamylase as described above. In some embodiments, at least 60%, at least 65%, at least 70%, at least 75%, at least 80%, at least 85%, at least 90%, at least 94%, at least 95%, at least 96%, at least 97%, at least 98% and even at least 99% of the dry solids of the granular starch is hydrolyzed. In some embodiments, the granular starch substrate is completely hydrolyzed. In some embodiments, at least 90% of the granular starch is hydrolyzed in 100 hours. In certain embodiments, at least 90% of the granular starch substrate is hydrolyzed in a time period of 24 hours. In other embodiments, at least 95% of the granular starch substrate is hydrolyzed in a time period of 24 hours.

The yield of glucose (percent of the total solubilized dry solids) may be at least about 85%, 90%, 91%, 92%, 93%, 94%, 95%, 96%, 97% and 98%. However, in a preferred embodiment, the glucose is continually produced and substantially all of the glucose is used in the process to produce an end-product, such as ethanol (reference is made to MOLECULAR STRUCTURE AND FUNCTION OF FOOD CARBOHYDRATE, ED. G. G. BIRCH ET AL, APPLIED SCIENCE PUBLISHERS, LONDON).

In some embodiments, the method involves a simultaneous saccharification and fermentation (SSF), wherein the hydrolysis step and a fermentation step are carried out contemporaneously. To affect saccharification and fermentation a glucoamylase is added to the slurry containing the granular starch substrate contacted with the *Rhizopus* spp. alpha-amylase. The *Rhizopus* spp. alpha-amylase and glucoamylase may be supplied separately or in combined form, and may be supplied as crude cell culture medium, cell-free filtrates, or purified enzymes. Alternatively, cells that express the *Rhizopus* spp. alpha-amylase and glucoamylase are added to the slurry.

In some embodiments, secondary enzymes including non-starch polysaccharide-hydrolyzing enzymes can be included with the glucoamylase during saccharification and/or fermentation, including but not limited to, cellulases, hemicellulases, xylanases, proteases, phytases, pullulanases, beta amylases, lipases, cutinases, pectinases, beta-glucanases, galactosidases, esterases, cyclodextrin transglycosyltransferases (CGTases), beta-amylases and combinations thereof.

The organism used in fermentations will depend on the desired end-product. Typically, if ethanol is the desired end product, yeast are used as the fermenting organism. In some embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Altech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time (e.g., to produce at least 10% ethanol from a substrate having between about 25 and about 40% DS in less than 72 hours). Yeast cells are generally supplied in amounts of about $10^4$ to about $10^{12}$, and, in some embodiments, from about $10^7$ to about $10^{10}$ viable yeast count per ml of fermentation broth. The use of yeast in fermentation is well known and reference is made to THE ALCOHOL TEXTBOOK, K. JACQUES ET AL., EDS. 1999, NOTTINGHAM UNIVERSITY PRESS, UK.

In some embodiments, the amount of ethanol produced by the present methods is at least about 8%, at least about 10%, at least about 12%, at least about 14%, at least about 15%, at least about 16%, at least about 17%, or even at least about 18% (v/v). Optionally, following fermentation, alcohol (e.g., ethanol) may be extracted, purified and recovered by methods well known in the art (e.g., distillation, ultra filtration, molecular sieve dehydration). The ethanol obtained according to process of the invention can be used as a fuel ethanol, portable ethanol, or industrial ethanol.

In further embodiments, by use of appropriate fermenting microorganisms as known in the art, the fermentation end product can include without limitation glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically, when lactic acid is the desired end product, a *Lactobacillus* sp. (*L. casei*) can be used; when glycerol or 1,3-propanediol are the desired end-products *E. coli* can be used; and when 2-keto-D-gluconate, 2,5-diketo-D-gluconate, and 2-keto-L-gulonic acid are the desired end products, *Pantoea citrea* can be used as the fermenting microorganism. The above enumerated list are only examples and one skilled in the art will be aware of a number of fermenting microorganisms that can be appropriately used to obtain a desired end product.

Additional aspects and embodiments of the compositions and methods will be apparent in view of the following examples, which should not be construed as limiting.

EXAMPLES

Figure 2:
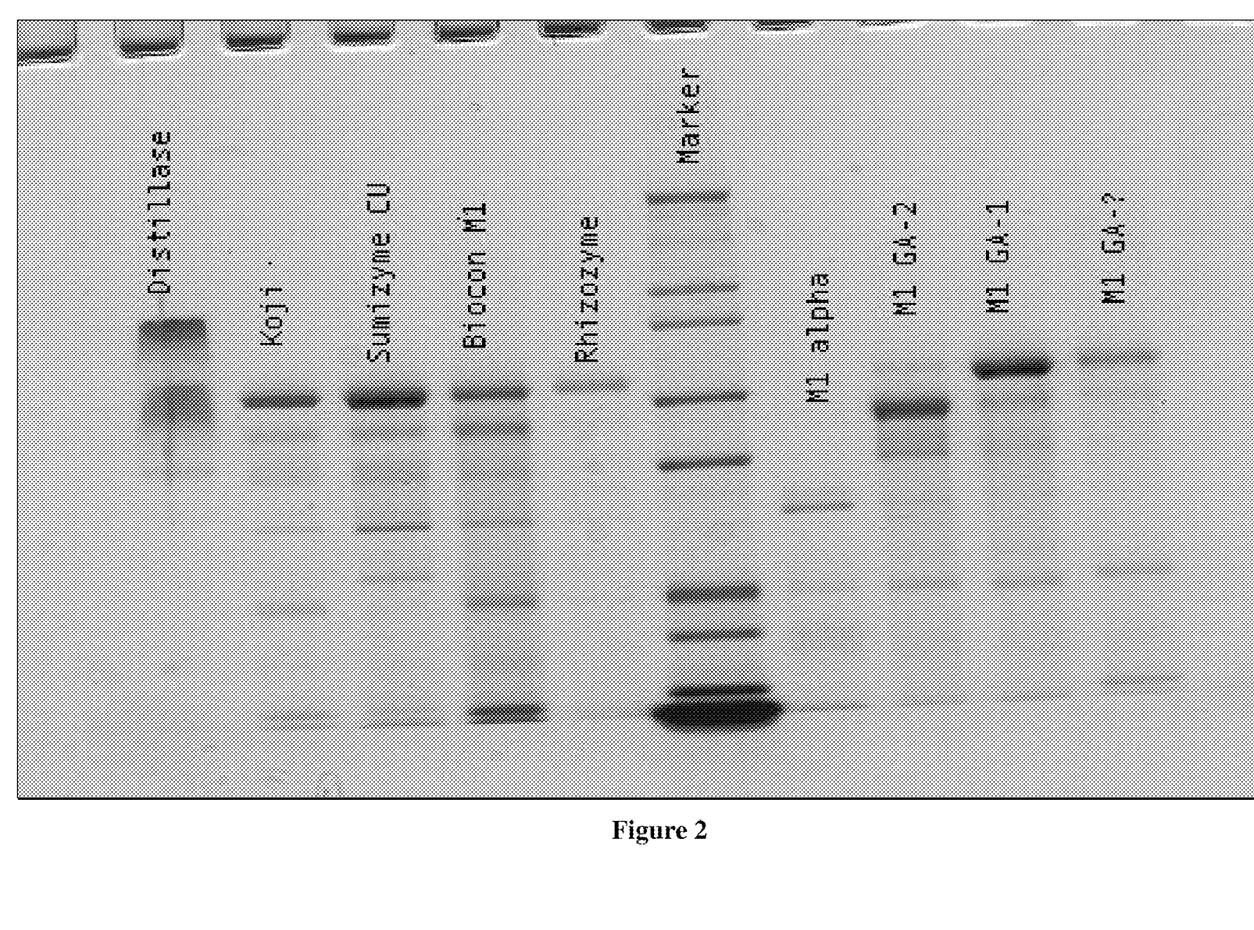
FIG. 2 is a SDS-PAGE including purified Rhizopus Amylase.

The following abbreviations are used herein: RoAA (a purified *Rhipozus* alpha-amylase composition having the sequence disclosed in SEQ ID NO: 1); TrGA (*Trichoderma reesei* glucoamylase; AkAA (*Aspergillus kawachi* alpha-amylase having the mature protein of sequence of SEQ ID NO: 3 as disclosed in FIG. 2 of U.S. Pat. No. 7,037,704); GA (glucoamylase); GAU (glucoamylase unit); AAU (alpha-amylase unit); wt % (weight percent); ° C. (degrees Centigrade); rpm (revolutions per minute); H$_2$O (water); dH$_2$O (deionized water); g or gm (grams); µg (micrograms); mg (milligrams); µL (microliters); ml or mL (milliliters); mm (millimeters); µm (micrometer); M (molar); mM (millimolar); µM (micromolar); U (units); V (volts); MW (molecular weight); sec (seconds); min(s) (minute/minutes); hr(s) (hour/hours); DO (dissolved oxygen); and EtOH (ethanol).

The following assays and methods are used in the examples provided, below:

Alpha-Amylase Activity

Alpha-amylase activity can be determined as soluble starch units (SSU) and is based on the degree of hydrolysis of soluble potato starch substrate (4% DS) by an aliquot of the enzyme sample at pH 4.5, 50° C. The reducing sugar content is measured using the DNS method as described in Miller, G. L. (1959) *Anal. Chem.* 31:426-428.

Alpha-amylase activity (AAU) was determined by the rate of starch hydrolysis, as reflected in the rate of decrease of iodine-staining capacity measured spectrophotometrically. One AAU of bacterial alpha-amylase activity is the amount of enzyme required to hydrolyze 10 mg of starch per min under standardized conditions.

Glucoamylase Activity

Glucoamylase activity in glucoamylase activity units (GAU) were determined using the PNPG assay. The PNPG assay is based on the ability of glucoamylase enzyme to catalyze the hydrolysis of p-nitrophenyl-alpha-D-glucopyranoside (PNPG) to glucose and p-nitrophenol. At an alkaline pH the nitrophenol forms a yellow color that is measured spectrophotometrically at 400 nm used in the calculation for GAU. One glucoamylase unit is the amount of enzyme that will liberate one gram of reducing sugars calculated as glucose from a soluble starch substrate per hour under the specified conditions of the assay.

Example 1

Purification of Alpha-Amylase from *Rhizopus* M1 Extract

Crude *Rhizopus* M1 enzyme extract was obtained from BioCon (Bangalore, India) as a dry powder. The extract was determined to include both alpha-amylase and glucoamylase activity, requiring fractionation.

Figure 1:
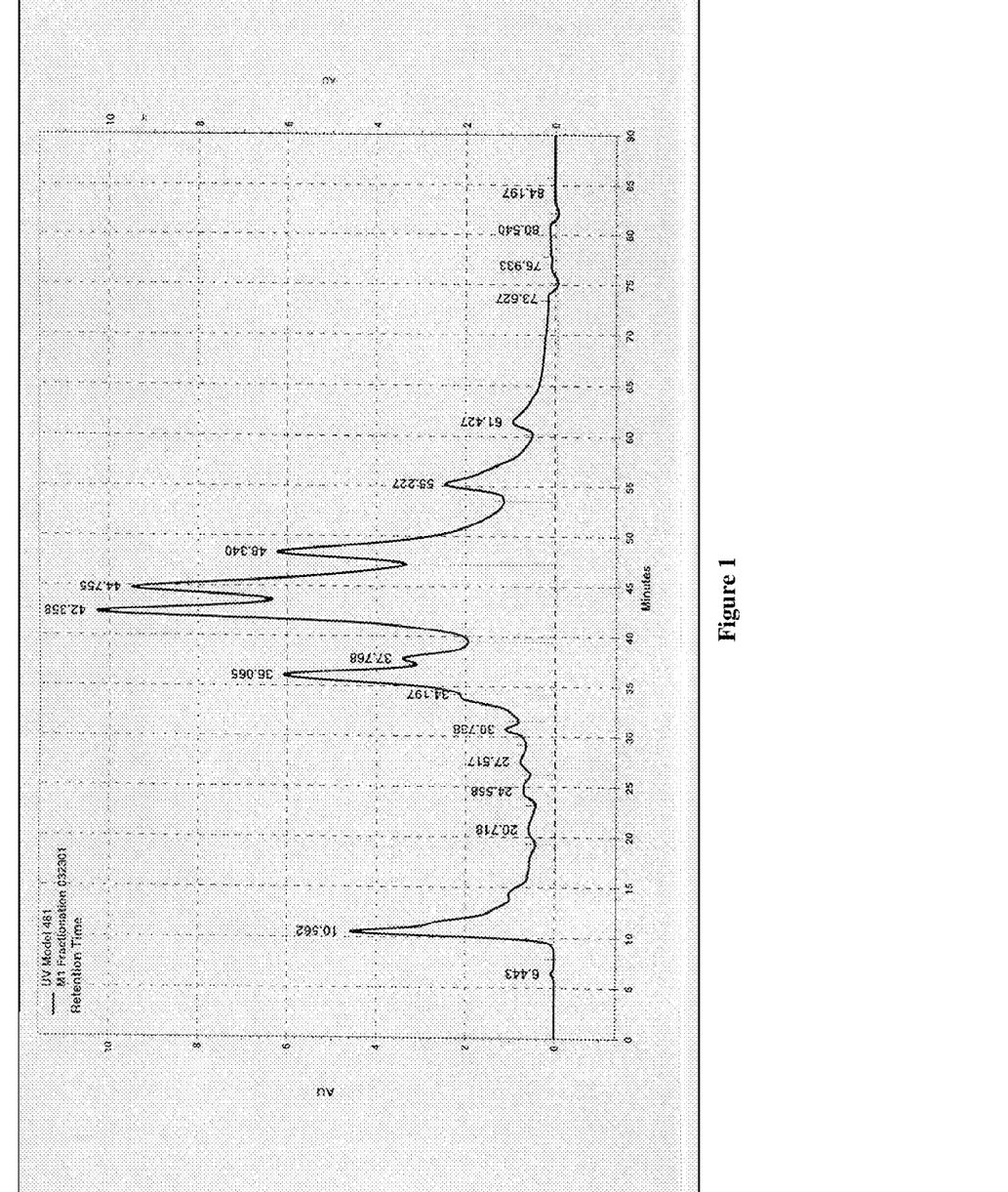
FIG. 1 is a chromatograph for POROS HQ (anion exchange) of Crude Rhizopus M1 enzyme extract.

Briefly, the powder was dissolved in water at a concentration of 40 g/L. 500 ml was applied to a 20×300 mm column of POROS HS (cation exchange) resin equilibrated to pH 5.0 with 10 mM sodium acetate. Alpha-amylase activity flowed through the column without binding, while the contaminating glucoamylase activity bound to the column and was removed. The alpha-amylase activity was collected and applied to a 20×300 mm column of POROS HQ (anion exchange) resin equilibrated to pH 5.0 with 10 mM sodium acetate. Again, the alpha-amylase activity flowed through the column without binding, while additional contaminating proteins bound to the column and were removed (FIG. 1). The alpha-amylase activity was collected and concentrated by ultrafiltration in an Amicon (Millipore Corp., Billerica, Mass.) stirred cell using a PES membrane with a 10,000 Dalton molecular weight cutoff.

Ammonium sulfate was added to the concentrated alpha-amylase activity containing column flow-through to a final concentration of 1.0 molar, and the material was applied to a column of POROS HP2 (hydrophobic resin) equilibrated with 10 mM sodium acetate pH 5.0, 1.0 M ammonium sulfate. As before, the alpha-amylase activity flowed through the column without binding, while contaminating proteins bound to the column and were removed. The alpha-amylase activity was collected and dialyzed against 10 mM sodium acetate. The purity of the preparation was assessed by Novex SDS-PAGE (Invitrogen, Carlsbad, Calif.) and estimated to be greater than 95% pure (see "M1 alpha" of FIG. 2). The amino acid sequence of the purified alpha-amylase (RoAA) was determined by standard methods and is presented as SEQ ID NO: 1.

Example 2

Figure 3:
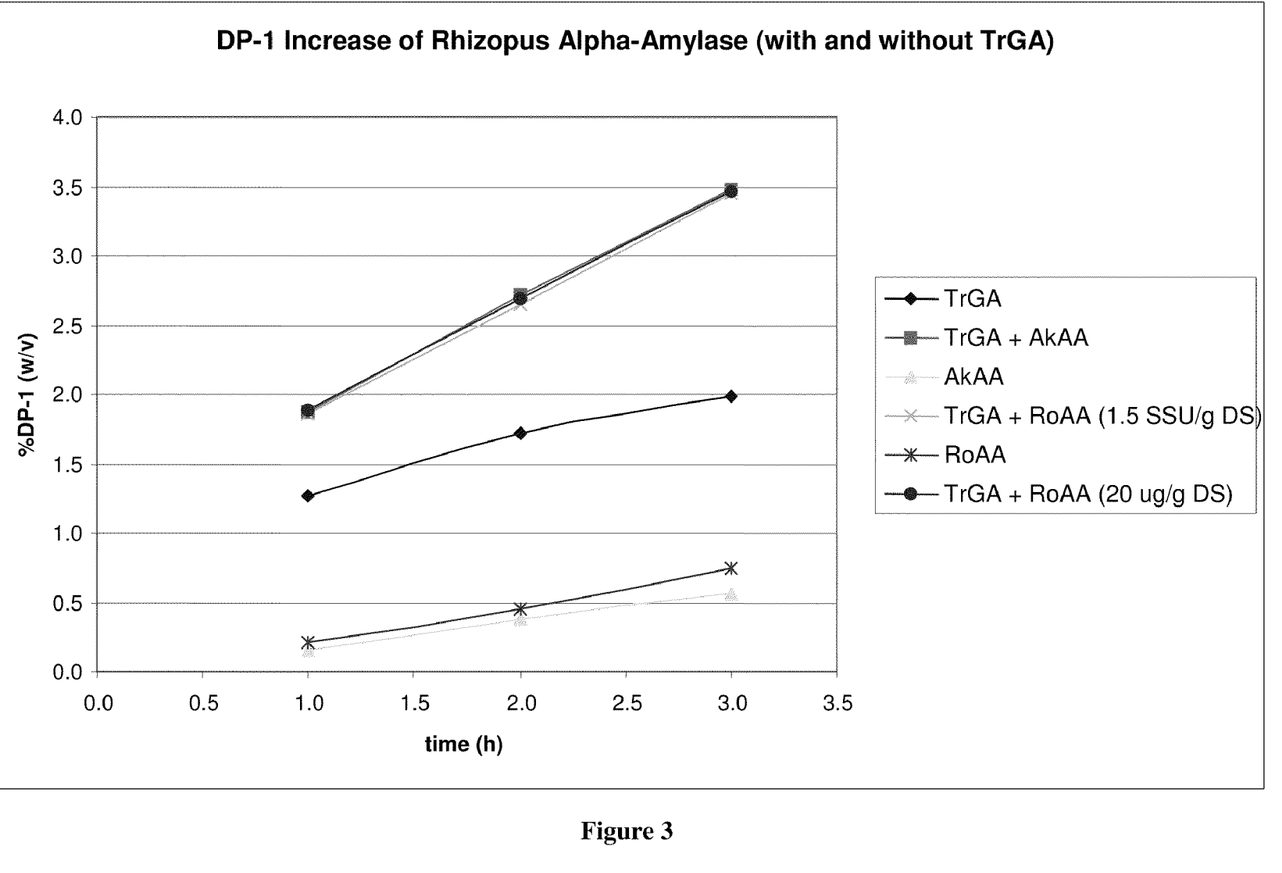
FIG. 3 is a graph showing the amount of glucose released (% DP-1 (w/v)) as a function of time (h) using *Trichoderma reesei* glucoamylase (TrGA), *Aspergillus kawachi* alpha-amylase (AkAA), *Rhizopus oryzae* alpha-amylase (RoAA), or combinations thereof.

Influence of RoAA and AkAA on Glucose Release from Raw Starch in Conjunction with TrGA RoAA was compared to *A. kawachi* alpha-amylase (AkAA) in a glucose release assay using raw corn starch as a substrate. The AkAA was dosed at 1.5 AAU/g dry solids and the RoAA was dosed on either an equal protein or equal activity basis to AkAA. In addition, the relative influence of the amylases on glucose release by *T. reesei* glucoamylase (TrGA) was determined. TrGA was dosed at 0.5 GAU/g dry solids either alone or in the presence of AkAA or RoAA. A 32% raw starch slurry was prepared and the pH of the slurry was adjusted to 4.2 with dilute sulfuric acid. This slurry was placed in a 32° C. water bath and gently mixed for 3 hours. At various time intervals, samples were taken for HPLC analysis. The glucose release was measured as % DP-1 (w/v). The results are shown in FIG. 3.

Example 3

Effect of RoAA During Simultaneous Saccharification and Fermentation (SSF)

Figure 4:
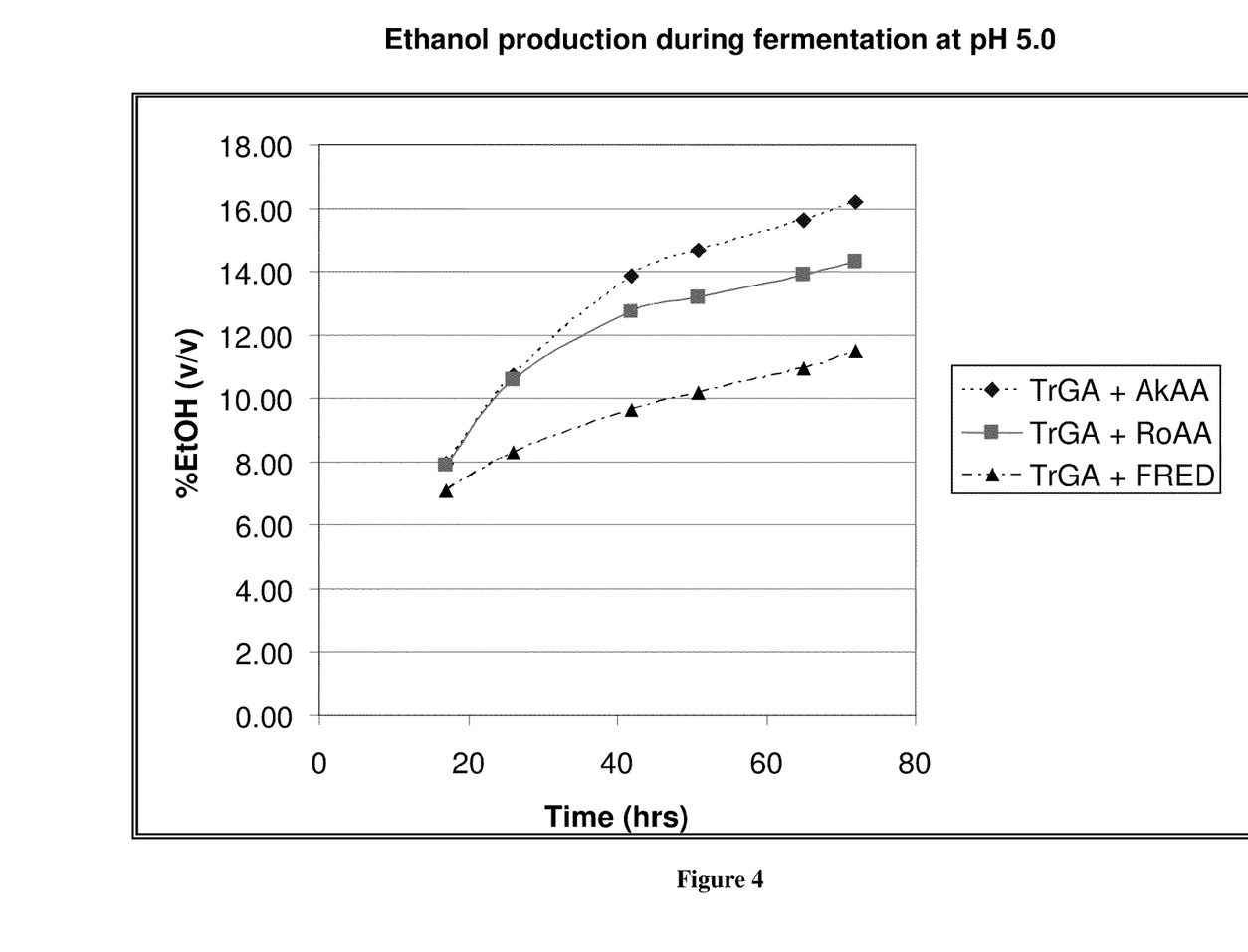
FIG. 4 is a graph showing ethanol produced (% EtOH (v/v)) as a function of time (h) during fermentation at pH 5.0.
Figure 5:
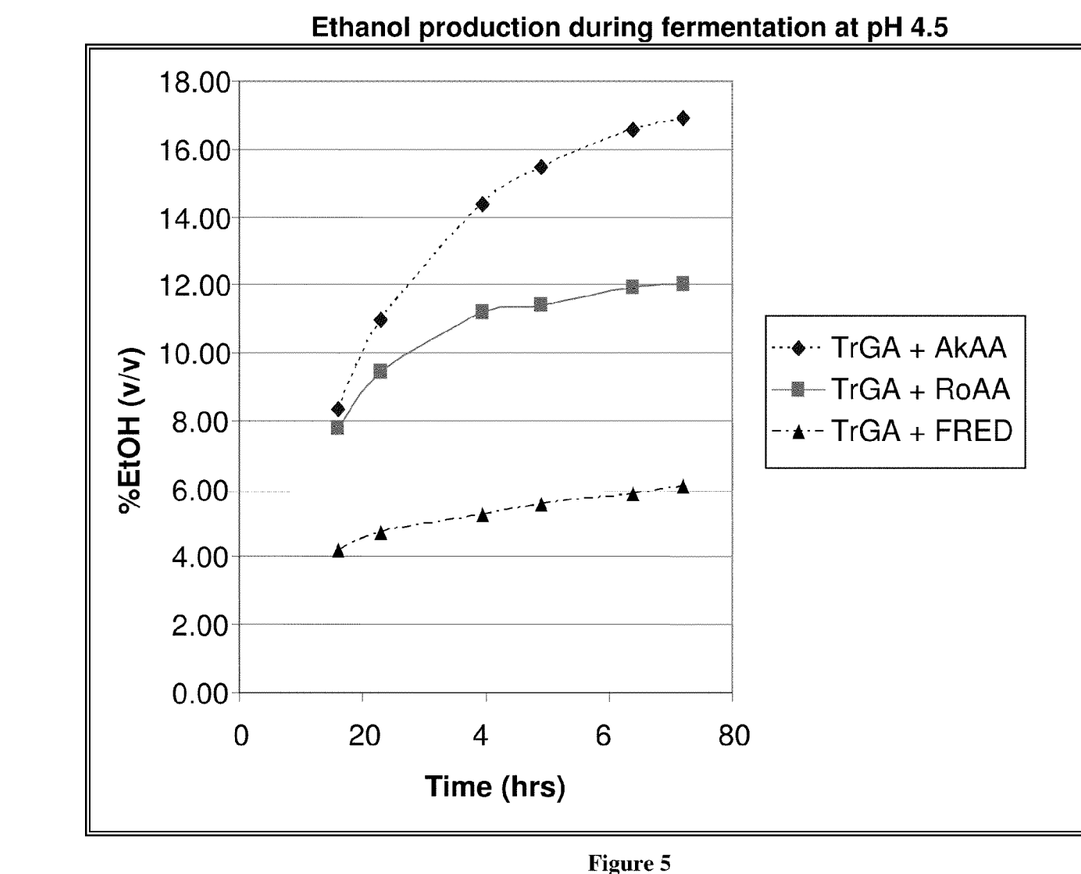
FIG. 5 is a graph showing ethanol produced (% EtOH (v/v)) as a function of time (h) during fermentation at pH 4.5.

RoAA was compared to AkAA and SPEZYME FRED (Genencor International Inc.) in a simultaneous saccharification and fermentation (SSF) of non-cooked whole ground corn substrate. The AkAA was dosed at 2.25 AAU/g dry solids and the RoAA and SPEZYME FRED were dosed on an equal protein basis to AkAA. The TrGA was dosed at 0.75 GAU/g dry solids. A 32% (ds) corn flour slurry was prepared containing 200 ppm urea and the pH of the slurry was adjusted to 4.5 or 5.0 with dilute sulfuric acid. Fermentations were carried out in 125 ml flasks containing 100 gm of mash (slurry). The desired levels of enzymes were added followed by 3 ml of propagated yeast slurry to start the fermentation. The yeast inoculum was prepared by adding 0.26 gm of dry Fali yeast to 100 gm of mash. This slurry was placed in a 32° C. water bath and gently mixed for about 17 hrs. At various time intervals samples of the fermentation were taken for HPLC analysis. The results are shown in FIGS. 4 and 5.

All references and publications cited herein are incorporated by reference in their entirety. The described aspects and embodiments of the compositions and methods are intended to be illustrative and not restrictive, and the skilled person will recognize additional aspect and embodiments. Headings are provided for convenience and descriptions provided under one heading apply throughout the document unless context clearly dictates otherwise.

What is claimed is:

1. A composition comprising a polypeptide component consisting essentially of an alpha-amylase and a glucoamylase, wherein the alpha-amylase is a *Rhizopus* alpha-amylase having at least 92% sequence identity to the amino acid sequence of SEQ ID NO: 1.

2. The composition of claim 1, wherein the *Rhizopus* alpha-amylase is the only granular starch hydrolyzing component in the composition.

3. The composition of claim 1, wherein the *Rhizopus* alpha-amylase is a recombinant alpha-amylase.

4. The composition of claim 1, wherein the *Rhizopus* alpha-amylase has the amino acid sequence of SEQ ID NO: 1.

5. The composition of claim 1, wherein the glucoamylase is a recombinant glucoamylase.

6. The composition of claim 1, wherein the glucoamylase is a *Rhizopus* glucoamylase.

7. The composition of claim 1, wherein the glucoamylase is a *Trichoderma, Aspergillus, Talaromyces*, or *Humicola* glucoamylase.

8. The composition of claim 1 further comprising an enzyme selected from the group consisting of a protease, a cellulase, a pullulanase, a second alpha-amylase, a glucoamylase, and combinations thereof.

9. A composition comprising a recombinant alpha-amylase and a glucoamylase, wherein the recombinant alpha-amylase is a *Rhizopus* alpha-amylase having at least 92% sequence identity to the amino acid sequence of SEQ ID NO: 1.

10. The composition of claim 9, wherein the alpha-amylase has the amino acid sequence of SEQ ID NO: 1.

11. The composition of claim 9, wherein the glucoamylase is a recombinant glucoamylase.

12. The composition of claim 9, wherein the glucoamylase is a *Rhizopus* glucoamylase.

13. The composition of clam 9, wherein the glucoamylase is a *Trichoderma, Aspergillus, Talaromyces*, or *Humicola* glucoamylase.

14. The composition of claim 9 further comprising an enzyme selected from the group consisting of a protease, a cellulase, a pullulanase, a second alpha-amylase, a glucoamylase, and combinations thereof.

15. A method of hydrolyzing granular starch comprising contacting a substrate containing granular starch with the composition of claim 1.

16. The method of claim 15, wherein the substrate is corn, wheat, sorghum, barley, rye, or a combination thereof.

17. The method of claim 15, wherein the substrate and the composition are incubated at a temperature and for a period of time sufficient to hydrolyze the granular starch.

* * * * *